United States Patent [19]

Favstritsky et al.

[11] Patent Number: 4,935,153

[45] Date of Patent: Jun. 19, 1990

[54] METHOD FOR THE CONTROL OF BIOFOULING IN RECIRCULATING WATER SYSTEMS

[75] Inventor: Nicalai A. Favstritsky, Lafayette; Arthur J. Hein, West Lafayette; Glade E. Squires, West Lafayette, all of Ind.

[73] Assignee: Great Lakes Chemical Corporation, West Lafayette, Ind.

[21] Appl. No.: 211,227

[22] Filed: Jun. 24, 1988

[51] Int. Cl.$^5$ .................................................. C02F 1/50
[52] U.S. Cl. .................................... 210/755; 210/764; 71/67; 162/161
[58] Field of Search ................... 210/754, 755, 764; 71/67; 162/161

[56] References Cited

U.S. PATENT DOCUMENTS 3,152,073 10/1964 Morton .................................. 210/62
4,297,224 10/1981 Macchiarolo et al. ............. 210/755

FOREIGN PATENT DOCUMENTS

WO88/02351 4/1987 PCT Int'l Appl. .

*Primary Examiner*—Tom Wyse
*Attorney, Agent, or Firm*—Kirkland & Ellis

[57] ABSTRACT

A method of controlling biofouling in an aqueous system comprising introducing into the system a biocidally effective amount of a water soluble perhalide of the formula:

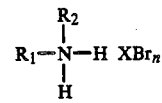

where $R_1$ and $R_2$ are hydrogen, hydroxyethyl, alkyl, cyclic alkyl, (alpha, omega)-alkyl, alkyl ether, polyether, heterocyclic ring-substituted alkyl, and halogenated alkyl; n is 2 to 6: X is chlorine, bromine or iodine; and only one of $R_1$ and $R_2$ may be hydrogen.

10 Claims, No Drawings

METHOD FOR THE CONTROL OF BIOFOULING IN RECIRCULATING WATER SYSTEMS

BACKGROUND OF THE INVENTION

1. Field of the Invention

The present invention discloses a novel method for the substantial elimination of the major cause of biofouling in recirculating water systems, in particular, those systems recirculating water for cooling purposes, such as, for example, water cooling towers, air conditioning systems, and the like.

2. Description of the Art

Biological fouling of circulating cooling water systems is a common problem resulting from excessive growth and development of different types of simple life forms (e.g., microorganisms such as algae, bacteria and fungi.) Circulating cooling water systems are excellent places for the incubation and growth of biological organisms because such systems contain nutrients (typically organic contamination) from air drawn into the system and from organic materials naturally occurring in the water. In addition, the water temperature in cooling towers is warm enough to provide an ideal incubation environment. Biological growth can foul pipelines, increase water circulating costs, cause and/or accelerate corrosion of metal, attack wood, and substantially reduce heat transfer thereby contributing to decreased efficiency of the cooling tower system.

Common forms of microorganisms found in a cooling tower system include algae, slime-forming fungi and bacteria, wood destroying organisms and sulfate reducing organisms along with many other forms of bacteria which may have little or no effect on cooling tower efficiency.

It is generally desirable that a biocide meet the following criteria:

(1) wide kill spectrum—the agent should be effective against a wide variety of microorganisms, such as, for example, algae, bacteria, fungi, mold and other aquatic organisms;
(2) fast rate of kill;
(3) low cost;
(4) useful in wide pH ranges;
(5) non-corrosive to metals and wood;
(6) compatible with commonly used cooling water treatment chemicals such as scale inhibitors and corrosion inhibitors:
(7) unaffected by organic contaminants or nitrogen compounds in the water recirculating system;
(8) ease in handling and application; and
(9) capable of obtaining appropriate federal and state governmental agency approval.

Biocides can be divided into two basic classifications: non-oxidizing and oxidizing biocides. In general, the non-oxidizing biocides function primarily by altering the permeability of the cell walls of the microorganisms and interfering with their biological processes. Common non-oxidizing biocides include organo-sulfur compounds, quaternary ammonium salts, chlorinated phenolics and heavy metal compounds.

Oxidizing biocides cause irreversible oxidation/hydrolysis of protein group in the microorganism and of the polysaccharides that bind the microorganisms to the surfaces of the cooling tower equipment. The result of this process is a loss of normal enzyme activity and cell death.

Oxidizing biocides heretofore proposed for cooling water use include:

(1) Chlorine;
(2) Bromine;
(3) Chloroisocyanurates;
(4) Chlorine dioxide;
(5) Hypochlorites;
(6) Bromine chloride and bromine-chlorine mixtures;
(7) 1-bromo-3-chloro-5,5-dimethylhydantoin ("BCDMH")

Each of these common biocides will be briefly discussed.

(1) Chlorine

Chlorine is probably the most common biocide in use for cooling tower treatment. It is generally an excellent algicide and bactericide although some strains of bacteria can develop chemical resistance to chlorine. Often chlorine must be used in a shock treatment system to provide good biocide performance. Gas chlorination equipment is costly and generally requires a relatively large capital investment. Normal use levels must be dramatically increased to maintain effectiveness when cooling water has become contaminated with hydrocarbons, ammonia and organic material.

Excessive chlorine concentrations have an adverse effect on cooling tower wood. Chlorine also tends to lower pH by its formation of HCl in water. Chlorine becomes less effective as a biocide above about pH 8.0–8.5 and becomes corrosive below about pH 6.5. Chlorine is a heavy greenish-yellowish gas with a suffocating odor. It requires special heavy and cumbersome steel cylinders under pressure to be transported. The recent industrial concern about industrial leaks and safety have made handling of chlorine cylinders even more suspect.

(2) Bromine

Liquid bromine has also been used in the treatment of biofouled cooling towers. However, bromine has not received widespread commercial acceptance, apparently because of handling difficulties and the cost of bromination equipment, as well as its low solubility in $H_2O$. (3.43 g/100 g water @ 30° C.)

| Vapor Pressure of Bromine: | |
|---|---|
| °C. | (mm Hg) |
| 20 | 173 |
| 25 | 214 |
| 30 | 264 |

(3) Chlorine Dioxide

Chlorine dioxide is usually classified as an oxidizing biocide although its kill mechanism is not oxidative. It is more effective at a higher pH or in nitrogen or organic contaminated systems than chlorine. Because it is an unstable compound, it is usually generated on-site with special equipment. It is also more expensive than chlorine.

(4) Chloroisocyanurates

Chloroisocyanurates are easily handled powdered compounds which hydrolyze in water to slowly release chlorine and cyanuric acid. However, they suffer all the drawbacks of chlorine in pH effectiveness ranges and present potential corrosion problems.

(5) Hypochlorites

Sodium and calcium hypochlorites function in much the same manner as chlorine gas but in an easier to handle form. However, hypochlorites have all the disadvantages of chlorine plus a higher cost. These products also tend to increase pH by the formation of metal hydroxides and additional reagents must be added to achieve control. There is also a concern of quick gassing when product is added to water. Liquid hypochlorites also suffer from quick decay rates of active agent because they are unstable.

(6) Bromine Chloride and Bromine-chlorine Mixtures

Bromine chloride, available only as a liquid under pressure, has found some favor as a biocide. It hydrolyzes completely in dilute aqueous solutions to hypobromous acid (HOBr) and hydrochloric acid (HCL). The hypobromous acid is an effective, potent biocide for algae and bacteria. Bromine chloride has generally not been promoted for use on industrial recirculating cooling towers because of the high cost for feed equipment and accessories. Mixtures of bromines and chlorine have also been investigated as biocides. Such mixtures may be applied as a liquid/gas mixture or in the form of sodium hypochlorite and sodium hypobromite. It has been reported that a bromine/chlorine mixture displays greater biocide activity than bromine or chlorine alone. The costs of handling, as well as the safety issues involved with such mixtures have prohibited their widespread use.

(7) BCDMH

BCDMH serves as an excellent biocide in recirculating cooling towers and other water systems. Its solid form makes it easy to handle and clean-up after, and its predominate use of bromine chemistry makes it very efficient where chlorine is not. However, there are certain conditions where BCDMH has limitations. The product has low solubility in cold water, requires specialized feeding equipment to optimize product dissolution and requires high pressure or expensive options to the equipment for large applications.

DISCUSSION OF BROMINE CHEMISTRY

Aqueous bromine has been proven to be a very effective biocide, particularly under alkaline (high pH) and high nitrogen concentration conditions. A brief discussion of the chemistries involved follows:

A. Bromine and chlorine hydrolyze in water according to the following:

$$Br_2 + H_2O \rightleftharpoons HOBr + H^{3O} + Br^- \quad (1)$$

$$Cl_2 + H_2O \rightleftharpoons HOCl + H^+ + Cl^- \quad (2)$$

Hypobromous acid (HOBr) and hypochlorous acid (HOCl) are the active biocides.

B. Under alkaline conditions the following reactions occur:

$$HOBr \rightarrow H^+ + OBr^- \quad (3)$$

$$HOCl \rightarrow H^+ + OCl^- \quad (4)$$

Both HOBr and HOCl are many times more effective biocide then their counterparts $OBr^- + OCl^-$.

Table 1 shows the relative concentrations of the hypohalous acids as a function of pH.

TABLE 1

| pH | % HOCl | % HOBr |
|---|---|---|
| 6 | 97 | 100 |
| 7 | 76 | 98 |
| 7.5 | 50 | 94 |

TABLE 1-continued

| pH | % HOCl | % HOBr |
|---|---|---|
| 8 | 24 | 83 |
| 8.5 | 9 | 60 |
| 9 | 3 | 33 |

C. Bromine and chlorine also differ in their reactions with nitrogen compounds. Both form haloamines (bromamines and chloramines) according to the following reactions:

$$HOBr + NH_2X \rightarrow NBrX_2 + H_2O \quad (5)$$

$$HOCl + NH_2X \rightarrow NClX_2 + H_2O \quad (6)$$

Chloramines are very poor biocides relative to hypochlorous acid. Bromamines on the other hand, are known to be almost as effective as hypobromous acid. An added benefit for environmental discharge concerns is that residual bromamines have a half life measured in minutes compared to many hours for chloramine.

Morton, U.S. Pat. No. 3,152,073 describes the use of tetramethylammonium chlorodibromide in sterilizing water. Morton goes on to disclose a wide variety of tetraalkylammonium polyhalides which contain alkyl groups of six or fewer carbons, suggesting that they may be used as single reagents, directly added to water, to achieve sterilization. It has now been found that, in fact, many of Morton's compounds are not sufficiently soluble in water for use by the method disclosed.

Gannon, et al., U.S. patent application Ser. No. 048,902, filed Apr. 20, 1987, discloses water sterilization compositions and methods using tetrasubstituted ammonium perhalides and certain trisubstituted amine hydrotribromides. The utility of these compositions and methods has been inhibited by the poor water solubility of the compounds.

Accordingly, a primary object of the present invention is the provision of method of water treatment involving the use of a novel biological control agent, or biocide which displays unique qualities when compared with other available biocides.

Another object is to provide a method of the character described that obviates the disadvantages of prior agents.

A further object is to provide a method of the character described which employs a novel stable, water soluble source of bromine.

SUMMARY OF THE INVENTION

The foregoing and other objects, advantages and features may be achieved with a novel method for treating biofouling problems inherent in recirculating water and other aqueous systems involving treatment of aqueous systems by introducing a biocidally effective amount of a water soluble organic ammonium perhalide of the formula:

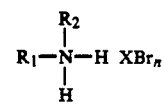

where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl; X is chlorine, bromine or iodine; n is 2 to 6; and only one of $R_1$ and $R_2$ may be hydrogen, into the water at a frequency, duration and concentration sufficient to control biofouling. Preferably, the perhalide is introduced in amounts sufficient to kill biofouling microorganisms at film forming surfaces of the system and thereafter to maintain the concentration of organic ammonium perhalide at a level sufficient to reduce substantially the regrowth of such microorganisms at such surfaces. Preferably, the organic ammonium perhalide is provided at a daily level of at least about 0.005 pound per thousand gallons of water in the system.

DETAILED DESCRIPTION OF THE PREFERRED EMBODIMENT

In accordance with the present invention it has been discovered that organic ammonium perhalides effectively control bacterial growth in cooling tower, water recirculating and other aqueous systems. By the present method, reduction in treatment costs (when compared to the prior art biocidal agents) may be achieved. Due to the nature of water cooling towers and recirculating systems in relation to microorganism growth environments, it is necessary to provide a method of treating the recirculating water which, on the one hand, kills microorganisms adhering to the walls and other structures of the system and, on the other hand, substantially reduces the potential for microorganism regrowth.

Accordingly, the method of the present invention involves treating aqueous systems by introducing a biocidally effective amount of a water soluble mono- or di- substituted ammonium perhalide of the formula:

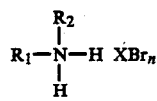

where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl: X is chlorine, bromine or iodine; n is 2 to 6; and only one of $R_1$ and $R_2$ may be hydrogen, into the water at a frequency, duration and concentration sufficient to control biofouling in the system.

Preferably, the perhalide is introduced in amounts sufficient to kill biofouling microorganisms at film forming surfaces of the system and thereafter to maintain the concentration of organic ammonium perhalide at a level sufficient to reduce substantially the regrowth of such microorganisms at such surfaces.

The water soluble organic ammonium perhalides that are useful in accordance with the method of the present invention are disclosed and claimed in copending Favstritsky, U.S. patent application entitled WATER SOLUBLE ORGANIC AMMONIUM PERHALIDES, Ser. No. 211,362, U.S. Pat. No. 4,886,915 filed herewith.

The solubility and bromine content of the compounds depend on the bulk and nature of the substituents. The most preferred substituents are $R_1$=hydroxyethyl, $C_1$ to $C_8$ alkyl groups, and $R_2$=hydrogen, hydroxyethyl, or $C_1$ to $C_8$ alkyl groups.

In general, the compounds used in accordance with the method of this invention are mono- and di-substituted perhalides where X may be chlorine or iodine. It is preferred, however, to employ compounds where X is bromine, that is, perbromides of the formula $R_1R_2NH_2$—$Br_3$.

Specific stable, water soluble perhalides useful with the method of the present invention include ethanolammonium perbromide, propylammonium perbromide, diethanolammonium perbromide, butylammonium perbromide, methylethanolammonium per bromide, ethylethanolammonium perbromide, hexylammonium perbromide octylammonium perbromide, dipropylammonium perbromide, dibutylammonium perbromide, diethylammonium perbromide, 1,6-hexanediammonium perbromide, as well as the corresponding chloro- and iodo-dibromides.

Ethanolammonium perbromide, HO—$C_2H_4$—$NH_3Br_3$, is the preferred water soluble organic ammonium perhalide in accordance with this invention.

Bromine is the active biocidal species in organic ammonium perbromides. It forms HOBr in the bulk water system to serve as the primary biocide. The uniqueness of these compounds is that the organic carrier serves as a solubilizer, allowing more bromine in the water to serve as a biocide. The complex formed also reduces vapor pressure, highly corrosive and toxic vapors and reduces severe skin contact burns that exist with bromine alone. The combination of the HBr serves as a pH stabilizer in the recirculating system. This helps keep water conditions more favorable (i.e., lower pH) for the formation of the more efficacious biocidal product HOBr. (Basic conditions lead to OBr formation which is a less efficient biocide).

The method of the present invention involves the use of organic ammonium perhalides as biocidal agents for selectively controlling bacterial growth in cooling tower and water recirculating systems. Typically, organic ammonium perhalides may be pumped into the recirculating water of the system or simply introduced in measured amounts by hand into the system.

Because of their excellent water solubility, organic ammonium perhalides may be fed in systems in a relatively easy fashion. It is necessary to incorporate compatible materials of construction into the feed systems with organic ammonium perhalides due to their strong oxidizing nature. Materials such as engineered plastics may be suitably used. The following equipment is understood well, is inexpensive and commercially viable for feeding liquid biocidal products.

1. Liquid Metering Pump
2. Eductors
3. Simply pour out of bottle.
4. Gravity Feed
5. Drip In
6. Spray Products such as dipropylammonium perbromide, dibutylammonium perbromide and diethylammonium perbromide, which are partially soluble in water or are soluble solids, may be fed with the same methods but require additional dissolving time prior to use.

Automated control systems that measure bromine residuals may also be incorporated with this product to very accurately control feed within specific residual ranges. The agent may be fed in bulk water or into a side-stream.

By way of example, the reaction of ethanolammonium perbromide in water is as follows:

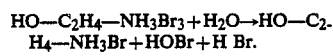

Organic ammonium perhalides exhibit:
(1) Excellent shelf life stability;
(2) Easy dispersability and solubiliity in water;
(3) Easy use with commercially available plastic head pumps and eductors and other low cost equipment.

In all cases, the presence of organic ammonium perhalides in the recirculating water acts as an effective biocide agent for controlling the growth of various bacteria on the surfaces of the recirculating water systems.

The amount of added organic ammonium perhalides necessary for adequate bacterial growth control is dependent upon a number of factors, among which include the volume of the recirculating system and the temperature and pH of the water therein, the location of the system (i.e., is the system located in an area where bacterial nutrients may easily enter the system), quality of make-up water, and the amount of bacterial growth present at the time treatment is started.

Thus, for a new recirculating system one may easily control bacterial growth by simply adding an amount of organic ammonium perhalide to the water and observing the results. That is, if after a period of time there is an observed build up of algae, bacteria, etc., the amount of organic ammonium perhalides should be increased. If there is no such build-up, the quantity of organic ammonium perhalide added may be reduced until an accumulation of bacteria is noted, at which time the organic ammonium perhalide level may be increased. Thus, through a series of "trial and error" tests the preferred quantity of organic ammonium perhalide needed for biomass control for any system can be easily established.

Generally organic ammonium perhalide is provided in sufficient quantity so that at least about 0.005 pound of agent is provided daily per thousand gallons of water in the system. In determining the proper amount of organic ammonium perhalide to be used, system volume is first ascertained. In the case of an open recirculating water system, system volume is normally calculated based on the amount of contained water plus daily make up for evaporation losses and daily blow down. Once the total volume is determined, the appropriate agent level may be selected, with the final level being optimized on a step-by-step basis in the described manner.

Preferably, organic ammonium perhalide is provided at a level lying in the range of about 0.01 to about 0.12 pounds per thousand gallons per day. The benefits of this invention may be achieved with larger amounts of agent (e.g., at levels as high as 0.6 pound per 1000 gallons of water or higher) although such higher quantities are typically only required where the system is quite dirty and then only for a relatively short period of time (e.g.. a few days to a few weeks).

Organic ammonium perhalide can also be applied very efficiently on a shock basis. Typical recommendations are to feed product for one hour intervals, 2 to 3 times per day. The main purpose of shock feeding is to use less chemical while maintaining an ever decreasing biocount. Organic ammonium perhalides can be provided at a rate lying in the range of about 0.6 to 7.2 lbs. per hour for every 1,000 gpm of flowing water. As needed, levels can be as high as 36 lb/hr for each 1000 gpm.

Ordinarily, biofouling is controlled by retaining a measurable halogen residual in the recirculating water (all day or for shocking interval) and without complete destruction of all microorganisms in the bulk water phase.

Unlike other water treatment environments such as swimming pools and the like, biocidal effectiveness in cooling tower and water recirculating systems is not dependent upon a complete biological kill of all microorganisms existing within the recirculating water. Rather, in cooling tower and water recirculating systems, it has been found in accordance with this invention that it is only necessary to substantially kill the microorganisms which adhere to the walls and other film forming structural surfaces of the system. Once such localized organisms are killed, the total microorganism count in the recirculating water is essentially irrelevant to the efficacy of the water treatment method; that is, as long as the microorganisms are in circulation in the system (i.e., not adhering to the walls or other structural surfaces of the system), there is no noticeable detrimental effect on the heat-exchange capacity of the system.

As a result, the novel method of the present invention does not have as its objective the complete eradication of all microorganisms from the recirculating water but, instead, is intended to remove microorganism growth and biofilm from the surfaces of the recirculating water system. Thus, the term "biocidally effective" as used herein should be understood to refer to the selective attack on biofilmforming organisms located at system surfaces but should not be understood to mean the substantial elimination of bulk water phase microorganisms. Other applications of the process of this invention include disinfection and other biological control of aqueous systems in the industrial and consumer home use, as follows:

INDUSTRIAL APPLICATIONS

Recirculating cooling water
Once-through cooling water
Wastewater
Brewery pasteurizer water
Air washer water
Evaporative cooling water
Air scrubber systems
Humidifier systems
Oilfield injection water
Pond and lagoon water
Degreaser disinfectants
Closed cooling system water
Irrigation system disinfection
Metal working system disinfection
Food plant disinfection
Bleaching—pulp and paper
Textile
Metal etching
Metal extraction.

CONSUMER APPLICATIONS

Toilet bowl cleaners/disinfectants
Hard surface cleaners/disinfectants
Air conditioning pan water
Decorative fountain water
Tile and group cleaners
Bleaching agent compositions
Dishwashing formulation
Laundry formulation
Pool biocontrol/disinfection
Spas and hot tub biocontrol/disinfection Thus, the term "aqueous system" as used herein encompasses all such systems.

Ethanolammonium perbromide and other organic ammonium perbromides can be used in different forms to meet various application criteria. For example, dilution with variable amounts of water, bases, acids, surfactants, salts, etc. and other solvents gives unique characteristics to the product to make a lower vapor pressure, reduce potency, make it easier to handle and stabilize.

In addition, stabilized aqueous solutions of the type disclosed in the copending Favstritsky application may also be employed. Thus, when the corresponding mono- or di-substituted ammonium hydrohalide, $R_1R_2NH_2X$, where $R_1$, $R_2$ and X are as previously defined, are mixed in aqueous solution with one mole of bromine, stabilized aqueous perbromide compositions are obtained. Shelf life stability of such aqueous solutions may also be enhanced by replacing a portion of the hydrohalide with an alkali metal or ammonium bromide stabilizing salt, especially sodium bromide or ammonium bromide. Preferably, the ratio of hydrohalide to other salt is abaout 1:1.

The agents of this invention may also be mixed with other active agents such as algacides, fungicides, corrosion inhibitors, scale inhibitors, nonoxidizing biocides and other compatible products which will lend greater functionality to the product. If soluble with the agents of this invention, such other additives may be incorporated in the same feed system. Insoluble products may be fed in a separate manner, or other additives can be incorporated to increase solubility.

EXPERIMENTAL EVALUATIONS

In order to establish the effectiveness of organic ammonium perhalides as water treatment biocides, biocidal agents, a series of tests have been performed. These tests document the use of organic ammonium perhalides in various sizes and types of cooling towers and water recirculating systems. Where practical, tests have been performed on similar cooling tower systems using BCDMH as a biocide so that a comparison of biocidal effectiveness with that known biocide can be made.

Other tests compare the biocidal efficacy of the family of perbromides vs. various organisms. *P. aeruginosa* is the primary bacteria of concern in recirculating systems. Ethanolammonium perbromide showed 100T kill vs. *P. aeruginosa* in 5 minutes @ 0.6 ppm $Cl_2$. The data are reported in Tables 2 and 3 for ethanol ammonium bromide ("EAPB"): propylammonium perbromide ("PAPB"): and diethanolammonium perbromide (DEAPB").

TABLE 2

| | Polyhalides vs. *P. aeruginosa* | | | |
| --- | --- | --- | --- | --- |
| CPD | mg Sample/ L $H_2O$ | Measured Free Halogen Residual as $Cl_2$ | Measured Total Halogen Residual as $Cl_2$ | Time to Kill |
| PAPB | 1.9 | 0.18 ppm | 0.33 ppm | 10 min. |
| EAPB | 1.76 | 0.21 ppm | 0.29 ppm | 10 min. |
| DEAPB | 1.71 | 0.32 ppm | 0.34 ppm | 10 min. |

TABLE 3

| | | Inhibition of Growth | | | |
| --- | --- | --- | --- | --- | --- |
| | | ppm | % Inhibition of Growth | | |
| Organism | Type | Product | PAPB | EAPB | DEAPB |
| *Klebsiella pneumoniae* | Bacteria | 20 | 76 | 92 | 81 |
| *Pseudomonas aeruginosa* | Bacteria | 20 | 95 | 99 | 99 |

TABLE 3-continued

| | | Inhibition of Growth | | | |
| --- | --- | --- | --- | --- | --- |
| | | ppm | % Inhibition of Growth | | |
| Organism | Type | Product | PAPB | EAPB | DEAPB |
| *Bacillus megaterium* | Bacteria | 20 | 61 | 99 | 97 |
| *Trichodema viride* | Fungus | 20 | 2 | 15 | 16 |
| *Chorella pyrenoidosa* | Algae | 10 | 27 | 53 | 29 |

NOTE: % Inhibition of Growth = $\frac{\text{\# cells killed}}{\text{initial \# of cells}} \times 100$ The efficacy of the organic ammonium perhalides of the invention has been demonstrated by the following examples.

EXAMPLE 1

Cooling Tower 1

Single Cooling Tower
Contained Volume: 15,000 gallons
Circulation Rate: 100 gpm.

This tower was controlled on a low level BCDMH feed. EAPB was shock fed (i.e.. adding high dose of product and turning off to allow biocide to do its job) periodically over an 8 hour day. All total halogen was detected based on feed amount and theoretical expected. Data are reported in Table 4.

TABLE 4

| | Example 1 Trial Data | | |
| --- | --- | --- | --- |
| Product Feed Rate (ml/min) | Time (Hours) | Total Halogen Measured as $Cl_2$ (ppm) | |
| | | Basin | Deck |
| 0.0 | 0.0 on | 0.0 | |
| 15.0 | 0.08 | 11.75 | |
| 15.0 | 0.25 | 22.39 | |
| 15.0 | 0.50 off | 40.05 | 30.10 |
| 0.0 | 1.0 | 23.75 | 24.10 |
| 0.0 | 1.5 | 20.27 | |
| 0.0 | 3.75 | 8.79 | 8.51 |
| 0.0 | 4.25 on | 7.09 | |
| 1.5 | 4.58 | 9.7 | |
| 1.5 | 5.08 | 11.63 | |
| 1.5 | 5.5 | 12.05 | |
| 1.5 | 5.9 | 12.76 | |
| 1.5 | 6.2 | 12.90 | |

The system cleaned all biomass and sludge out based on high level feed and showed that EAPB is very effective as a quick shocker as well as completely miscible in water. Bromine residuals were generated in water in accordance with its theoretical "load" of oxidizing halogen; the yield was very close to the expected amount. With respect to its microbiological efficacy, bromine thus delivered is not distinguishable from that which is derived from inorganic sources. There is virtually no interference in efficacy from the organic carriers at use-concentration dilutions.

The concentrations of product required for efficacous application must be determined from the percent available bromine and knowledge of the halogen demand in the system. Generally, a concentration of one ppm free residual bromine will disinfect (i.e., 99.9% kill in 10 minutes) laboratory strains of *Pseudomonas aeruginosa*. However, continuous-dosing at one to three ppm free residual bromine is recommended for applications in which there is a constant influent source of microorganisms, or in systems where biofilms are predominant.

Slug-dosing treatment protocols are especially efficacous in troublesome systems: the product water solubility allows for convenient application. Five ppm free residual bromine slug-doses for 1-2 hrs once per day are recommended.

Based on this test, it was observed that:

1. EAPB is an efficient source of bromine, all bromine introduced into the system could be accounted for due to its excellent water solubility.

2. EAPB could be easily dispensed by liquid pumps, commonly used in industry, and a steady residual will be maintainable based on cooling tower size as well as system demand. No problems were seen from the slight vapor pressure the product possesses.

3. EAPB also has the advantage of being very effective as a shock treatment.

4. At even the extreme levels run in this test, no foaming from the amine was evident.

EXAMPLE 2

Cooling Tower 2

Chemical Plant Tower:
Contained System Volume: 35,000 gallons
Circulation Rate: 1000 gpm.

This tower had previously been treated with BCDMH with about 11.5 pounds of product per day and an erratic residual $Cl_2$ control of 1.3 to 2.5 ppm. (1 ppm BCDMH has a raw dose of 0.55 ppm active $Cl_2$) This high level Cl could lead to excessive corrosion as well as over use of biocide. The EAPB controlled the system accurately at 0.05 to 0.4 ppm during its 6 week trial at a feed of 6.1# or 0.4 gallons of product per day. (1 ppm ethanolammonium perbromide has a raw dose of 0.181 Active $Cl_2$.) BCDMH control was 1.7 mls/year for mild steel coupons. Data are given in Tables 5 and 6.

TABLE 5

Average Background Conditions for Example 2

|  | BCDMH | EAPB |
|---|---|---|
| Daily Water Use (gallons) | 4,800 | 17,000 |
| Calcium (ppm) | 76 | 103 |
| Alkalinity | 71 | 43 |
| Conductivity | 496 | 630 |
| Phosphate (ppm) | 17 | 10 |
| Bromide (ppm) | 26 | 80 |
| Chloride (ppm) | 31 | 23 |
| TOC (ppm) | 61 | — |
| DMH (ppm) | 73 | — |
| pH | 7.7 | 7.1 |
| Free $Cl_2$ (ppm) | 0.6 | 0.10 |
| Total $Cl_2$ (ppm) | 1.63 | 0.14 |
| Colony Counts | $<10^3$ | $10^5$ |
| lbs/Day Feed | 8.6 | 6.1 |
| Avg. Dosage (ppm $Cl_2$) | 118 ppm | 7.8 ppm |

TABLE 6

Example 2 Trial Data

| Day | (ppm) | Colony Counts | (ppm) | Colony Counts |
|---|---|---|---|---|
| 1 | 1.33 | $10^3$ | 0.31 | $10^4$ |
| 2 | 1.45 | $<10^3$ | 0.27 | $10^4$ |
| 3 | 1.15 | $10^3$ | 0.36 | $10^3$ |
| 4 | 1.54 | $<10^3$ | 0.20 | $10^4$ |
| 5 | 1.31 | $10^3$ | 0.21 | $10^4$ |
| 6 | 1.88 | $<10^3$ | 0.24 | $10^5$ |
| 7 | 2.53 | $<10^3$ | 0.23 | $10^5$ |
| 8 | 1.70 | $<10^3$ | 0.22 | $10^5$ |
| 9 | 1.77 | $<10^3$ | 0.06 | $10^5$ |
| 10 | 1.97 | $<10^3$ | 0.12 | $10^5$ |
| 11 | 1.50 | $<10^3$ | 0.22 | $10^5$ |
| 12 | 1.54 | $<10^3$ | 0.13 | $10^5$ |
| 13 | 1.50 | $10^3$ | 0.07 | $10^5$ |
| 14 | | | 0.04 | $10^5$ |
| 15 | | | 0.05 | $10^5$ |
| 16 | | | 0.05 | $10^5$ |
| 17 | | | 0.06 | $10^5$ |
| 18 | | | 0.05 | $10^5$ |
| 19 | | | 0.04 | $10^5$ |
| 20 | | | 0.08 | $10^4$ |
| 21 | | | 0.11 | $10^4$ |
| 22 | | | 0.05 | $10^6$ |
| 23 | | | 0.11 | $10^6$ |
| Average | 1.63 | $<10^3$ | 0.14 | $10^5$ |
| Dose (lbs./day) | 8.6 | | 6.1 | |

A second test was performed at the end of the trial to increase feed of EAPB and an increased biocontrol was achieved as expected, as reported in Table 7. Colony counts (count bacteria/ml) were determined using Selecticult dip slide culture tests, a commercially available test for monitoring and enumerating microbiol densities in industrial fluids.

TABLE 7

Increase of EAPB Dosage for Example 2

| Day | Hour | Dose (lb/day) | Total $Cl_2$ (ppm) | Colony Counts Hot Side | Tower Deck |
|---|---|---|---|---|---|
| 23 | 1 am | 6.1 | .06 | $10^6$ | $10^5$ |
|  | 4 am | 6.1 | .11 | | |
|  | 8 am | 6.1 | .12 | | |
|  | 12 am | 6.1 | .13 | | |
|  | 2 pm | 16.5 | .17 | $10^5$ | $10^4$ |
|  | 4 pm | 16.5 | .19 | $10^5$ | $10^4$ |
|  | 8 pm | 16.5 | .24 | | |
|  | 12 pm | 16.5 | .27 | | |
|  | 4 am | 16.5 | .29 | | |
|  | 8 am | 16.5 | .30 | $10^6$ | $10^4$ |
|  | 10 am | 27.6 | .30 | $10^5$ | $10^4$ |
|  | 12 am | 27.6 | .33 | $10^5$ | $10^4$ |
|  | 4 pm | 27.6 | .33 | $10^5$ | $10^4$ |
|  | 8 pm | 27.6 | .36 | | |
|  | 12 pm | 27.6 | .42 | | |
|  | 4 am | 27.6 | .36 | $10^4$ | $10^4$ |
|  | 8 am | 27.6 | .42 | | |

I claim:

1. A method for controlling biofouling in an aqueous system comprising the steps of:

introducing a water soluble ammonium perhalide of the formula:

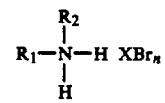

where $R_1$ and $R_2$ are independently hydrogen, hydroxyethyl, alkyl, cycloalkyl, alkyl ether, polyoxyalkylene, and halogenated alkyl; X is chlorine, bromine or iodine; n is 2 to 6; and only one of $R_1$ and $R_2$ may be hydrogen, into the system at a frequency, duration and concentration sufficient to control biofouling in the system.

2. A method, as claimed in claim 1, wherein X is bromine.

3. A method, as claimed in claim 2, wherein $R_1$ is a member selected from the group consisting of hydrogen, hydroxyethyl and $C_{1-8}$ alkyl and $R_2$ is a member selected from the group consisting of hydroxyethyl and $C_{1-8}$ alkyl.

4. A method, as claimed in claim 1, wherein the perhalide is ethanolammonium perbromide, $HOCH_2CH_2NH_3$—$Br_3$.

5. A method, as claimed in claim 1, wherein the perhalide is propylammonium perbromide, $CH_3CH_2CH_2NH_3$—$Br_3$.

6. A method, as claimed in claim 1, wherein the perhalide is diethanolammonium perbromide, $(HOCH_2CH_2)_2NH_2$—$Br_3$.

7. A method, as claimed in claim 1, wherein the aqueous system is a recirculating water system.

8. A method, as claimed in claim 7, wherein the water soluble ammonium perhalide is provided at a level of at least about 0.005 pounds per thousand gallons of water per day.

9. A method, as claimed in claim 8, wherein the perhalide is provided at a level of about 0.01 to 0.6 pounds per thousand gallons per day.

10. A method, as claimed in claim 8, wherein the aqueous system is shock treated by periodically providing water soluble ammonium perbromide at a rate of about 0.6 to 36 pounds per hour per thousand gallons per minute of flowing water.

* * * * *

UNITED STATES PATENT AND TRADEMARK OFFICE
CERTIFICATE OF CORRECTION

PATENT NO. : 4,935,153

DATED : June 19, 1990

INVENTOR(S) : Nicolai A. Favstritsky, et al.

It is certified that error appears in the above-identified patent and that said Letters Patent is hereby corrected as shown below:

In the portion of the cover sheet that lists the inventors' names, "Nicalai A. Favstritsky" should be --Nicolai A. Favstritsky--

Column 3, line 46     "$Br_2 + H_2O \rightleftarrows HOBr + H^{30} + Br^-$" should be --$Br_2 + H_2O \rightleftarrows HOBr + H^+ + Br^-$--

Column 6, lines 66-67     "$HO-C_2H_4-NH_3Br_3 + H_2O \rightarrow HO-C_2H_4-NH_3Br + HOBr + H\ Br.$" should be --$HO-C_2H_4-NH_3Br_3 + H_2O \rightarrow HO-C_2H_4-NH_3Br + HOBr + H\ Br$--

Column 8, line 61     "group" should be --grout--

Column 9, line 46     "100T" should be "100%"

Signed and Sealed this

Fifteenth Day of October, 1991

Attest:

HARRY F. MANBECK, JR.

*Attesting Officer*      *Commissioner of Patents and Trademarks*